(12) United States Patent
Na

(10) Patent No.: US 12,232,800 B2
(45) Date of Patent: Feb. 25, 2025

(54) ELECTRICALLY BASED MEDICAL TREATMENT DEVICE AND METHOD

(71) Applicant: Serendia, LLC, Lake Forest, CA (US)

(72) Inventor: Jongju Na, Songpa-Gu (KR)

(73) Assignee: Serendia, LLC, Lake Forest, CA (US)

( * ) Notice: Subject to any disclaimer, the term of this patent is extended or adjusted under 35 U.S.C. 154(b) by 0 days.

(21) Appl. No.: 18/679,893

(22) Filed: May 31, 2024

(65) Prior Publication Data

US 2024/0315762 A1 Sep. 26, 2024

Related U.S. Application Data

(63) Continuation of application No. 17/686,405, filed on Mar. 3, 2022, now abandoned, which is a
(Continued)

(30) Foreign Application Priority Data

Jun. 14, 2011 (KR) .......................... 10-2011-0057691
Jun. 14, 2011 (KR) .......................... 10-2011-0057692

(51) Int. Cl.
*A61B 18/14* (2006.01)
*A61B 18/00* (2006.01)
(Continued)

(52) U.S. Cl.
CPC ....... *A61B 18/1477* (2013.01); *A61H 39/002* (2013.01); *A61H 39/086* (2013.01); *A61N 1/0502* (2013.01); *A61N 1/06* (2013.01); *A61N 1/328* (2013.01); *A61B 2018/00452* (2013.01); *A61B 2018/0047* (2013.01); *A61B 2018/00589* (2013.01); *A61B 2018/00625* (2013.01); *A61B 2018/0072* (2013.01);
(Continued)

(58) Field of Classification Search
CPC .............. A61B 18/1477; A61H 39/002; A61H 39/086; A61N 1/0502; A61N 1/06; A61N 1/328
See application file for complete search history.

(56) References Cited

U.S. PATENT DOCUMENTS

| 6,277,116 B1 | 8/2001 | Utely et al. |
| 6,766,202 B2 | 7/2004 | Underwood et al. |

(Continued)

FOREIGN PATENT DOCUMENTS

| KR | 100719395 B1 | 5/2007 |
| KR | 100852500 B1 | 8/2008 |

(Continued)

OTHER PUBLICATIONS

IPR2024-00386, *Jeisys v. Serendia*; U.S. Pat. No. 8,142,426 B2 (Knopp), Exhibit 2058, (35 pages).
(Continued)

*Primary Examiner* — Amanda K Hulbert
*Assistant Examiner* — Philip C Edwards
(74) *Attorney, Agent, or Firm* — Danielson Legal LLC

(57) ABSTRACT

Embodiments of medical treatment including skin treatment using electrical energy, especially with the primary purpose for skin treatment for aesthetics are described generally herein. Other embodiments may be described and claimed.

17 Claims, 7 Drawing Sheets

Related U.S. Application Data continuation of application No. 17/061,523, filed on Oct. 1, 2020, now Pat. No. 11,406,444, which is a continuation of application No. 16/111,616, filed on Aug. 24, 2018, now Pat. No. 10,799,286, which is a continuation of application No. 15/202,511, filed on Jul. 5, 2016, now Pat. No. 10,058,379, which is a continuation of application No. 14/006,930, filed as application No. PCT/KR2012/004695 on Jun. 14, 2012, now Pat. No. 9,480,836.

(51) Int. Cl.
*A61B 18/12* (2006.01)
*A61H 39/00* (2006.01)
*A61H 39/08* (2006.01)
*A61N 1/05* (2006.01)
*A61N 1/06* (2006.01)
*A61N 1/32* (2006.01)

(52) U.S. Cl.
CPC .............. *A61B 2018/00726* (2013.01); *A61B 2018/00732* (2013.01); *A61B 2018/00738* (2013.01); *A61B 2018/00767* (2013.01); *A61B 2018/126* (2013.01); *A61B 2018/143* (2013.01); *A61B 2018/1475* (2013.01)

(56) References Cited

U.S. PATENT DOCUMENTS

| | | |
|---|---|---|
| 6,770,071 B2 | 8/2004 | Woloszko et al. |
| 6,890,319 B1 | 5/2005 | Crocker |
| 7,824,394 B2 | 11/2010 | Manstein |
| 8,012,153 B2 | 9/2011 | Woloszko et al. |
| 8,142,426 B2 | 3/2012 | Knopp et al. |
| 8,540,705 B2 | 9/2013 | Mehta |
| 8,608,737 B2 | 12/2013 | Mehta et al. |
| 8,900,231 B2 | 12/2014 | Kreindel |
| 9,095,358 B2 | 8/2015 | Woloszko et al. |
| 9,510,899 B2 | 12/2016 | Manstein |
| 10,799,285 B2 | 10/2020 | Mulholland |
| 10,869,812 B2 | 12/2020 | Na |
| 2002/0120260 A1 | 8/2002 | Morris et al. |
| 2002/0120261 A1 | 8/2002 | Morris et al. |
| 2003/0130711 A1 | 7/2003 | Pearson et al. |
| 2003/0195593 A1* | 10/2003 | Ingle ...................... A61N 1/403 607/116 |
| 2004/0058882 A1 | 3/2004 | Eriksson et al. |
| 2005/0222565 A1* | 10/2005 | Manstein ............ A61B 18/1477 606/41 |
| 2006/0036210 A1 | 2/2006 | Zhang et al. |
| 2007/0208340 A1 | 9/2007 | Ganz et al. |
| 2008/0082090 A1 | 4/2008 | Manstein |
| 2008/0091182 A1 | 4/2008 | Mehta |
| 2009/0093749 A1* | 4/2009 | Shalev ...................... A61K 8/46 604/20 |
| 2010/0204695 A1* | 8/2010 | Mehta ................ A61B 18/1206 606/42 |
| 2011/0288543 A1 | 11/2011 | Cheng et al. |

FOREIGN PATENT DOCUMENTS

| | | |
|---|---|---|
| KR | 200441552 Y1 | 8/2008 |
| WO | WO2007064718 A2 | 6/2007 |
| WO | WO2008005477 A2 | 1/2008 |
| WO | WO2010016848 A1 | 2/2010 |

OTHER PUBLICATIONS

IPR2024-00386, *Jeisys v. Serendia*; Berube et al, A Predictive Model, Laser in Surgery and Medicine; Exhibit 2060, (6 pages).
IPR2024-00386, *Jeisys v. Serendia*; Sylfirm Video2.mov, "Victory of Life, ViOL"; Exhibit 2063.
IPR2024-00386, *Jeisys v. Serendia*; Transcript of Sylfirm Video2; Exhibit 2064, (1 page).
IPR2024-00386, *Jeisys v. Serendia*; Braun, Sylfirm X article; Exhibit 2066, (3 pages).
IPR2024-00386, *Jeisys v. Serendia*; World-Class Product of Korea 2020 Certificate to ViOL (Dec. 9, 2020); Exhibit 2067, (1 page).
IPR2024-00386, *Jeisys v. Serendia*; Allure article, A New Filler for Laugh Lines & More Procedures That Are Safe for Dark Skin; Exhibit 2069, (10 pages).
IPR2024-00386, *Jeisys v. Serendia*; Vincent A. Thomas CV; Exhibit 2070, (17 pages).
IPR2024-00386, *Jeisys v. Serendia*; Daniel W. van de Weide CV; Exhibit 2072, (43 pages).
IPR2024-00386, *Jeisys v. Serendia*; C.L. Brace, Microwave ablation with a Triaxial Antenna Results in Ex Vivo Bovine Liver, vol. 53, No. 1, Jan. 2005; Exhibit 2073, (6 pages).
IPR2024-00386, *Jeisys v. Serendia*; D. Haemmerich, Finite-Element Analysis of Hepatic Multiple Probe Radio-Frequency Ablation, vol. 49, No. 7, Jul. 2002; Exhibit 2074, (7 pages).
IPR2024-00386, *Jeisys v. Serendia*; L. Zilberti, Charge Relaxation in Biological Tissues with Extremely High Permittivity, published on May 24, 2016; Exhibit 2075, (7 pages).
IPR2024-00386, *Jeisys v. Serendia*; pt. 1 IEC Int'l Standard, Medical Electrical Equipment—Part 2-2 (6.0 ed); Exhibit 2076, (190 pages).
IPR2024-00386, *Jeisys v. Serendia*; IEC Int'l Standard, Medical Electrical Equipment—Part 2-2 (5.0 ed—Withdrawn); Exhibit 2077, (166 pages).
IPR2024-00386, *Jeisys v. Serendia*; Abstract—IEC Int'l Standard, Medical Electrical Equipment—Part 2-2 (5.0 ed—Withdrawn); Exhibit 2078, (1 page).
IPR2024-00386, *Jeisys v. Serendia*; Sylfirm X (product information); Exhibit 2079, (5 pages).
IPR2024-00386, *Jeisys v. Serendia*; ViOL, Sylfirm X User Manual; Exhibit 2083, (43 pages).
IPR2024-00386, *Jeisys v. Serendia*; Sylfirm X Product Photographs; Exhibit 2086, (11 pages).
IPR2024-00386, *Jeisys v. Serendia*; D. van der Weide, Presentation—RF Microneedle Arrays: Thermal Results; Exhibit 2087, (12 pages).
IPR2024-00386, *Jeisys v. Serendia*; Photographs—Accused Product Examinations (Jun.-Aug. 2023); Exhibit 2088, (44 pages).
IPR2024-00386, *Jeisys v. Serendia*; Product photo (CX-3378C.1); Exhibit 2091, (1 page).
IPR2024-00386, *Jeisys v. Serendia*; Product photo (CX-3379C.1); Exhibit 2092, (1 page).
IPR2024-00386, *Jeisys v. Serendia*; Product photo (CX-3380C.1); Exhibit 2093, (1 page).
IPR2024-00386, *Jeisys v. Serendia*; Product photo (CX-3381C.1); Exhibit 2094, (1 page).
IPR2024-00386, *Jeisys v. Serendia*; Shin & Kim, Radiofrequency in Clinical Dermatology, accepted on Nov. 8, 2013; Exhibit 2095, (9 pages).
IPR2024-00386, *Jeisys v. Serendia*; Ahn & Cho, Invasive Pulse-Type, Bipolar, Alternating Current Radiofrequency Treatment using Microneedle Electrodes for Nasal Rosacea, accepted on Jun. 12, 2017; Exhibit 2096, (5 pages).
IPR2024-00386, *Jeisys v. Serendia*; Sylfirm X Introduction Video 1.mp4, "New X Tips"; Exhibit 2097.
IPR2024-00386, *Jeisys v. Serendia*; Transcript of Sylfirm X Introduction Video 1; Exhibit 2098, (1 page).
IPR2024-00386, *Jeisys v. Serendia*; Sylfirm X Introduction Video 2.mov, "Victory of Life, ViOL"; Exhibit 2099.
IPR2024-00386, *Jeisys v. Serendia*; Transcript of Sylfirm X Introduction Video 2; Exhibit 2100, (1 page).
IPR2024-00386, *Jeisys v. Serendia*; Press Release—BENEV Launches Sylfirm X Ultimate Edition (Apr. 26, 2021); Exhibit 2101, (4 pages).
IPR2024-00386, Declaration of Vincent A. Thomas in Support of Patent Owner's Preliminary Response (*Ilooda Co., Ltd and Jeisys Medical Inc. v. Serendia, LLC*; U.S. Pat. No. 9,480,836), (8 pages).
IPR2024-00384, Patent Owner's Preliminary Response, (*Jeisys Medical Inc. and Ilooda Co., Ltd. v. Serendia, LLC*; U.S. Pat. No. 9,320,536), Apr. 24, 2024 (82 pages).

(56) References Cited

OTHER PUBLICATIONS

IPR2024-00384, Patent Owner Serendia LLC's Motion to Seal, (*Jeisys Medical Inc. and Ilooda Co., Ltd.* v. *Serendia, LLC*; U.S. Pat. No. 9,320,536), Apr. 24, 2024 (10 pages).
IPR2024-00384, *Jeisys* v. *Serendia*; Complainant's Jul. 24, 2023 Supplemental Validity Contentions, Case 337-TA-1356, Exhibit 2003, (425 pages).
IPR2024-00384, *Jeisys* v. *Serendia*; Expert Report of Jean Woloszko, Case 337-TA-1356, Exhibit 2004, (684 pages).
IPR2024-00384, *Jeisys* v. *Serendia*; Deposition transcript of Jean Woloszko taken Sep. 14, 2023, Case 337-TA-1356, Exhibit 2007, (2 pages).
IPR2024-00384, *Jeisys* v. *Serendia*; Deposition transcript of Jean Woloszko taken Sep. 15, 2023, Case 337-TA-1356, Exhibit 2008, (2 pages).
IPR2024-00384, *Jeisys* v. *Serendia*; Complainant's Public Interest Statement & Complaint of Serendia, Case 337-TA-__, Exhibit 2016, (74 pages).
IPR2024-00384, *Jeisys* v. *Serendia*; The Parties' Proposed Procedural Schedule and Notice of Proceedings and state and federal litigation pursuant to order No. 3, Case 337-TA-1356, Exhibit 2017, (26 pages).
IPR2024-00384, *Jeisys* v. *Serendia*; Order No. 6 Adopted Procedural Schedule dated Apr. 27, 2023, Case 337-TA-1356, Exhibit 2018, (12 pages).
IPR2024-00384, *Jeisys* v. *Serendia*; Respondents' Joint Reply Post-Hearing Brief, Case 337-TA-1356, Exhibit 2019, (6 pages).
IPR2024-00384, *Jeisys* v. *Serendia*; Response of Ilooda to the Complaint and Notice of Investigation, Case 337-TA-1356, Exhibit 2020, (88 pages).
IPR2024-00384, *Jeisys* v. *Serendia*; Jeisys and Cynosure's Response to the Complaint and Notice of Investigation, Case 337-TA-1356, Exhibit 2021, (68 pages).
IPR2024-00384, *Jeisys* v. *Serendia*; Letter from Merle W. Richman to Cutera dated Mar. 20, 2018, Exhibit 2022, (1 page).
IPR2024-00384, *Jeisys* v. *Serendia*; Letter from Keith K. Im to Cynosure dated Nov. 29, 2021, Exhibit 2023, (2 pages).
IPR2024-00384, *Jeisys* v. *Serendia*; Order No. 33 Granting Parties' Joint Motion to Amend the Amended Procedural Schedule dated Oct. 19, 2023, Case 337-TA-1356, Exhibit 2024, (5 pages).
IPR2024-00384, *Jeisys* v. *Serendia*; Brochure Sylfirm X Dual Wave RF Microneedling System, Exhibit 2037, (16 pages).
IPR2024-00384, *Jeisys* v. *Serendia*; Respondents' Notice of Prior Art, Case 337-TA-1356, Exhibit 2053, (11 pages).
IPR2024-00384, *Jeisys* v. *Serendia*; Sylfirm X Revolutionizes Clinical Applications of RF Microneedling dated May/Jun. 2022, Exhibit 2066, (3 pages).
IPR2024-00384, *Jeisys* v. *Serendia*; World-Class Product of Korea 2020 Certificate to ViOL dated Dec. 9, 2020, Exhibit 2067, (1 page).
IPR2024-00384, *Jeisys* v. *Serendia*; Vincent A. Thomas CV, Exhibit 2070, (17 pages).
IPR2024-00384, *Jeisys* v. *Serendia*; ViOL, Sylfirm X User Manual, Exhibit 2083, (43 pages).
IPR2024-00384, *Jeisys* v. *Serendia*; Sylfirm X Product Photographs, Exhibit 2086, (11 pages).
IPR2024-00384, *Jeisys* v. *Serendia*; Sylfirm X Introduction Video 1.mp4, "New X Tips", Exhibit 2097.
IPR2024-00384, *Jeisys* v. *Serendia*; Transcript of Sylfirm X Introduction Video 1 "Sylfirm X. New X Tips", Exhibit 2098, (1 page).
IPR2024-00384, *Jeisys* v. *Serendia*; Deposition Transcript of Peter Crosby taken Sep. 4, 2023, Case 337-TA-1356, Exhibit 2103, (2 pages).
IPR2024-00384, *Jeisys* v. *Serendia*; Deposition Transcript of Peter Crosby taken Sep. 5, 2023, Case 337-TA-1356, Exhibit 2104, (2 pages).
IPR2024-00384, *Jeisys* v. *Serendia*; U.S. Patent Application Publication No. 20020120260 A1, Exhibit 2108, (67 pages).
IPR2024-00384, *Jeisys* v. *Serendia*; Certified English translation of Korean Registered Patent Publication No. KR10-0852500, Exhibit 2110, (11 pages).

IPR2024-00384, *Jeisys* v. *Serendia*; Respondents' Amended Notice of Prior Art, Case 337-TA-1356, Exhibit 2111, (11 pages).
IPR2024-00384, *Jeisys* v. *Serendia*; U.S. Pat. No. 6,890,319 B1, Exhibit 2115, (18 pages).
IPR2024-00384, *Jeisys* v. *Serendia*; U.S. Pat. No. 10,869,812 B2, Exhibit 2116, (32 pages).
IPR2024-00384, *Jeisys* v. *Serendia*; U.S. Pat. No. 8,540,705 B2, Exhibit 2117, (51 pages).
IPR2024-00384, *Jeisys* v. *Serendia*; USPTO File History for U.S. Pat. No. 10,869,812, Exhibit 2118, (733 pages).
IPR2024-00384, *Jeisys* v. *Serendia*; U.S. Pat. No. 6,277,116 B1, Exhibit 2119, (22 pages).
IPR2024-00384, *Jeisys* v. *Serendia*; U.S. Patent Application Publication No. 20020120261 A1, Exhibit 2120, (62 pages).
IPR2024-00384, *Jeisys* v. *Serendia*; Cartessa Aesthetics, Innovation in RF Microneedling: A closer look at VirtueRF, Jun. 2021, Exhibit 2122, (4 pages).
IPR2024-00384, *Jeisys* v. *Serendia*; Woloszko Hearing Transcript dated Nov. 7, 2023, Case 337-TA-1356, Exhibit 2125, (69 pages).
IPR2024-00384, *Jeisys* v. *Serendia*; Crosby Hearing Transcript dated Dec. 12, 2023, Case 337-TA-1356, Exhibit 2126, (31 pages).
IPR2024-00384, *Jeisys* v. *Serendia*; Crosby Opening Expert Report—Appendix 17, Exhibit 2127, (11 pages).
IPR2024-00384, *Jeisys* v. *Serendia*; Deposition transcript of Jongju Na dated Jul. 25, 2023, Case 337-TA-1356, Exhibit 2128, (5 pages).
IPR2024-00384, *Jeisys* v. *Serendia*; Sylfirm X Product Photographs, Exhibit 2130, (4 pages).
IPR2024-00384, *Jeisys* v. *Serendia*; U.S. Patent Application Publication No. 20060036210A1, Exhibit 2132, (69 pages).
IPR2024-00384, Declaration of Peter Crosby in Support Of Patent Owner's Preliminary Response, (*Jeisys Medical Inc. and Ilooda Co., Ltd.* v. *Serendia, LLC*; U.S. Pat. No. 9,320,536), Exhibit 2134 (65 pages).
IPR2024-00384, Declaration of Vince Thomas in Support of Patent Owner's Preliminary Response, (*Jeisys Medical Inc. and Ilooda Co., Ltd.* v. *Serendia, LLC*; U.S. Pat. No. 9,320,536), Exhibit 2135 (8 pages).
IPR2024-00384, *Jeisys* v. *Serendia*; Peter Crosby CV, Exhibit 2136, (8 pages).
IPR2024-00384, *Jeisys* v. *Serendia*; Appendix 5—Summary Invalidity Claim Chart; U.S. Pat. No. 9,320,536, Case 337-TA-1356, Exhibit 2137, (5 pages).
IPR2024-00384, *Jeisys* v. *Serendia*; USPTO Statutory Disclaimer dated Apr. 19, 2024, U.S. Appl. No. 13/825,083, Exhibit 2138, (11 pages).
IPR2024-00386, Patent Owner's Preliminary Response (*Ilooda Co., Ltd and Jeisys Medical Inc.* v. *Serendia, LLC*; U.S. Pat. No. 9,480,836), Apr. 25, 2024 (87 pages).
IPR2024-00386, Patent Owner Motion to Seal (*Ilooda Co., Ltd and Jeisys Medical Inc.* v. *Serendia, LLC*; U.S. Pat. No. 9,480,836), Apr. 25, 2024 (10 pages).
IPR2024-00386, *Jeisys* v. *Serendia*; Complainant's Jul. 24, 2023 Supplemental Validity Contentions, Case 337-TA-1356, Exhibit 2003, (425 pages).
IPR2024-00386, *Jeisys* v. *Serendia*; Expert Report of Jean Woloszko, Case 337-TA-1356, Exhibit 2004, (684 pages).
IPR2024-00386, *Jeisys* v. *Serendia*; Deposition transcript of Jean Woloszko taken Sep. 14, 2023, Case 337-TA-1356, Exhibit 2007, (2 pages).
IPR2024-00386, *Jeisys* v. *Serendia*; Deposition transcript of Jean Woloszko taken Sep. 15, 2023, Case 337-TA-1356, Exhibit 2008, (2 pages).
IPR2024-00386, *Jeisys* v. *Serendia*; Deposition transcript of Daniel W. van der Weide taken Aug. 31, 2023, Case 337-TA-1356, Exhibit 2009, (2 pages).
IPR2024-00386, *Jeisys* v. *Serendia*; Deposition transcript of Daniel W. van der Weide taken Sep. 1, 2023, Case 337-TA-1356, Exhibit 2010, (2 pages).
IPR2024-00386, *Jeisys* v. *Serendia*; Deposition transcript of David J. Goldberg taken Sep. 15, 2023, Case 337-TA-1356, Exhibit 2011, (2 pages).
IPR2024-00386, *Jeisys* v. *Serendia*; Hearing transcript held Nov. 7, 2023, Case 337-TA-1356, Exhibit 2012, (18 pages).

(56) References Cited

OTHER PUBLICATIONS

IPR2024-00386, *Jeisys* v. *Serendia*; Hearing transcript held Dec. 12, 2023, Case 337-TA-1356, Exhibit 2013, (9 pages).
IPR2024-00386, *Jeisys* v. *Serendia*; Hearing transcript held Dec. 11, 2023, Case 337-TA-1356, Exhibit 2014, (14 pages).
IPR2024-00386, *Jeisys* v. *Serendia*; Complainant's Public Interest Statement & Complaint of Serendia, Case 337-TA-_, Exhibit 2016, (74 pages).
IPR2024-00386, *Jeisys* v. *Serendia*; The Parties' Proposed Procedural Schedule and Notice of Proceedings and State and Federal Litigation Pursuant To Order No. 3, Case 337-TA-1356, Exhibit 2017, (26 pages).
IPR2024-00386, *Jeisys* v. *Serendia*; Order No. 6 Adopted Procedural Schedule, Case 337-TA-1356, Exhibit 2018, (12 pages).
IPR2024-00386, *Jeisys* v. *Serendia*; Respondents' Joint Reply Post-Hearing Brief, Case 337-TA-1356, Exhibit 2019, (6 pages).
IPR2024-00386, *Jeisys* v. *Serendia*; Response of Ilooda to the Complaint and Notice of Investigation, Case 337-TA-1356, Exhibit 2020, (88 pages).
IPR2024-00386, *Jeisys* v. *Serendia*; Jeisys and Cynosure's Response to the Complaint and Notice of Investigation, Case 337-TA-1356, Exhibit 2021, (68 pages).
IPR2024-00386, *Jeisys* v. *Serendia*; Letter from Merle W. Richman to Cutera dated Mar. 20, 2018, Exhibit 2022, (1 page).
IPR2024-00386, *Jeisys* v. *Serendia*; Letter from Keith K. Im to Cynosure dated Nov. 29, 2021, Exhibit 2023, (2 pages).
IPR2024-00386, *Jeisys* v. *Serendia*; Order No. 33 Granting Parties' Joint Motion to Amend the Amended Procedural Schedule dated Oct. 19, 2023, Case 337-TA-1356, Exhibit 2024, (5 pages).
IPR2024-00386, *Jeisys* v. *Serendia*; Ex. A-02 Invalidity Claim Chart, U.S. Pat. No. 9,480,836, Case 337-TA-1356, Exhibit 2025, (65 pages).
IPR2024-00386, *Jeisys* v. *Serendia*; U.S. Pat. No. 6,766,202 B2 (Underwood), Exhibit 2026, (16 pages).
IPR2024-00386, *Jeisys* v. *Serendia*; U.S. Pat. No. 9,095,358 B2 (Woloszko), Exhibit 2027, (20 pages).
IPR2024-00386, *Jeisys* v. *Serendia*; U.S. Pat. No. 8,012,153 B2 (Woloszko), Exhibit 2028, (32 pages).
IPR2024-00386, Declaration of Daniel W. Van Der Weide in Support of Patent Owner's Preliminary Response (*Ilooda Co., Ltd and Jeisys Medical Inc.* v. *Serendia, LLC*; U.S. Pat. No. 9,480,836), Exhibit 2030 (70 pages).
IPR2024-00386, Declaration of David J. Goldberg in Support of Patent Owner's Preliminary Response (*Ilooda Co., Ltd and Jeisys Medical Inc.* v. *Serendia, LLC*; U.S. Pat. No. 9,480,836), Exhibit 2031 (36 pages).
IPR2024-00386, Na, Jongju et al., "Electromagnetic Initiation and Propagation of Bipolar Radiofrequency Tissue Reactions via Invasive Non-Insulated Microneedle Electrodes", published on Nov. 13, 2015, IPR2024-00386, Exhibit 2032, (9 pages).
IPR2024-00386, *Jeisys* v. *Serendia*; Hearing transcript held Dec. 11, 2023; Case 337-TA-1356, Exhibit 2033, (4 pages).
IPR2024-00386, *Jeisys* v. *Serendia*; U.S. Patent Appl. Publ. No. 20110288543 A1 (Cheng), Exhibit 2034, (19 pages).
IPR2024-00386, *Jeisys* v. *Serendia*; Deposition transcript of Jongju Na taken Jul. 24, 2023; Case 337-TA-1356, Exhibit 2035, (4 pages).
IPR2024-00386, *Jeisys* v. *Serendia*; Letter from Long H. Chen-S, FDA dated Jun. 17, 2022, Exhibit 2036, (10 pages).
IPR2024-00386, *Jeisys* v. *Serendia*; Brochure Sylfirm X Dual Wave RF Microneedling System, Exhibit 2037, (16 pages).
IPR2024-00386, *Jeisys* v. *Serendia*; ViOL Patent List, https://violmedical.com/about/patent; Exhibit 2038, (2 pages).
IPR2024-00386, *Jeisys* v. *Serendia*; Sylfirm X Video.mov, "A New Paradigm for RF Micro-Needling"; Exhibit 2039.
IPR2024-00386, *Jeisys* v. *Serendia*; Transcript of Exhibit 2039—Sylfirm X Video; Exhibit 2040, (1 page).
IPR2024-00386, *Jeisys* v. *Serendia*; Kevin A. Wilson, Leading Regenerative Therapies Creating a Paradigm Shift in Aesthetic Medicine; Exhibit 2042, (9 pages).
IPR2024-00386, *Jeisys* v. *Serendia*; Sylfirm X testimonials; Exhibit 2043, (1 page).
IPR2024-00386, *Jeisys* v. *Serendia*; ViOL, Sylfirm X Clinical Paper Summary; Exhibit 2044, (34 pages).
IPR2024-00386, *Jeisys* v. *Serendia*; S.B. Cho et al., In Vivo Skin Reactions from Pulsed-Type, bipolar, alternating current radiofrequency treatment using invasive noninsulated electrodes; Exhibit 2045, (8 pages).
IPR2024-00386, *Jeisys* v. *Serendia*; You Jin Jung et al., Therapeutic Effects of a new invasive pulsed-type bipolar radiofrequency for facial erythema associated with acne vulgaris and rosacea, published on Mar. 2, 2021; Exhibit 2046, (6 pages).
IPR2024-00386, *Jeisys* v. *Serendia*; Shaun Wootten et al., An Evaluation of Electrocoagulation and thermal diffusion following radiofrequency microneedling using an in vivo porcine skin model, accepted on Aug. 4, 2020; Exhibit 2047, (7 pages).
IPR2024-00386, *Jeisys* v. *Serendia*; Yoram Harth et al., Depressed Acne Scars—Effective, Minimal Downtime Treatment with a Novel Smooth, Motion Non-Insulated Microneedle Radiofrequency Technology, accepted on Jun. 25, 2014; Exhibit 2048, (83 pages).
IPR2024-00386, *Jeisys* v. *Serendia*; U.S. Pat. No. 9,510,899 B2 (Manstein), Exhibit 2049, (14 pages).
IPR2024-00386, *Jeisys* v. *Serendia*; U.S. Pat. No. 6,770,071 B2 (Woloszko), Exhibit 2050, (66 pages).
IPR2024-00386, *Jeisys* v. *Serendia*; U.S. Patent Appl. Publ. No. 20080082090 A1, Exhibit 2051, (15 pages).
IPR2024-00386, *Jeisys* v. *Serendia*; Respondents' Notice of Prior Art; Case 337-TA-1356, Exhibit 2053, (11 page).
IPR2024-00386, *Jeisys* v. *Serendia*; Curriculum Vitae of David J. Goldberg, Exhibit 2055, (22 pages).
IPR2024-00386, *Jeisys* v. *Serendia*; Hee Kyung Kim et al., Immediate and Late Effects of Pulse Widths and Cycles on Bipolar, Gated Radiofrequency-Induced Tissue Reactions in in vivo Rat Skin, published on Mar. 25, 2023; Exhibit 2056, (10 pages).
IPR2024-00386, *Jeisys* v. *Serendia*; S. Tyler et al., Radiofrequency in Cosmetic Dermatology, vol. 24, No. 12, Dec. 2011; Exhibit 2057, (10 pages).
510k Summary—K082391; Primaeva Medical Inc., RX-0486, 2009, 5 Pages.
Berube et al., "A Predictive Model of Minimally Invasive Bipolar Fractional Radiofrequency Skin Treatment", Lasers in Surgery and Medicine 41:473-478 (2009), RX-1567, 6 Pages.
Berube et al., "A Predictive Model of Minimally Invasive Bipolar Fractional Radiofrequency Skin Treatment", Lasers in Surgery and Medicine 41:473-478 (2009), CX-0752, 6 Pages.
Alexiades-Armenakas et al., "Blinded, Randomized, Quantitative Grading Comparison of Minimally Invasive, Fractional Radiofrequency and Surgical Face-lift to Treat Skin Laxity", Arch Dermatol. 2010; vol. 146(4):396-405, 10 Pages.
D & PS, Magazine for Dermatologists & Plastic Surgeons, Nexgen®, 2010, CX-2622, 13 Pages.
Primaeva Medical Instructions, Primaeva Medical Inc., Miratone™ System, Exhibit# Berube 9, Jul. 26, 2023, 27 Pages.
Primaeva Medical User Manual, Exhibit# Berube 10, CX-0946, Jul. 26, 2023, 39 Pages.
Scarlett Website, CX-2612, Jan. 10, 2011, 16 Pages.
Shim Dku Thesis, "How Fractional micro-needle RF Works and How it Affects Skin Tissue", Department of Medical Laser, 2010, 57 Pages.
Evidentiary Hearing with excerpts dated Dec. 11, 2023; vol. 5, Case 337-TA-1356, 161 Pages.
Evidentiary Hearing with excerpts dated Dec. 12, 2023; vol. 6, Case 337-TA-1356, 144 Pages.
Evidentiary Hearing with excerpts dated Nov. 1, 2023; vol. 1, Case 337-TA-1356, 144 Pages.
Evidentiary Hearing with excerpts dated Nov. 2, 2023; vol. 2, Case 337-TA-1356, 114 Pages.
Evidentiary Hearing with excerpts dated Nov. 6, 2023; vol. 3, Case 337-TA-1356, 76 Pages.
Evidentiary Hearing with excerpts dated Nov. 7, 2023; vol. 4, Case 337-TA-1356, 271 Pages.

(56) References Cited

OTHER PUBLICATIONS

IPR2024-00463, Patent Owner's Preliminary Response (*Jeisys Medical Inc. v. Serendia, LLC*; U.S. Pat. No. 10,869,812), May 22, 2024 (84 pages).
IPR2024-00463, Patent Owner Motion To Seal (*Jeisys Medical Inc. v. Serendia, LLC*; U.S. Pat. No. 10,869,812), May 22, 2024 (9 pages).
IPR2024-00463, *Jeisys v. Serendia*; Complainant's Jul. 24, 2023 Supplemental Validity Contentions, Case 337-TA-1356, Exhibit 2003, (425 pages).
IPR2024-00463, *Jeisys v. Serendia*; Expert Report of Jean Woloszko, Case 337-TA-1356, Exhibit 2004, (684 pages).
IPR2024-00463, *Jeisys v. Serendia*; Deposition transcript of Jean Woloszko taken Sep. 14, 2023, Case 337-TA-1356, Exhibit 2007, (2 pages).
IPR2024-00463, *Jeisys v. Serendia*; Deposition transcript of Jean Woloszko taken Sep. 15, 2023, Case 337-TA-1356, Exhibit 2008, (2 pages).
IPR2024-00463, *Jeisys v. Serendia*; Complainant's Public Interest Statement & Complaint of Serendia, Case 337-TA-_, Exhibit 2016, (74 pages).
IPR2024-00463, *Jeisys v. Serendia*; The Parties' Proposed Procedural Schedule and Notice of Proceedings and State and Federal Litigation Pursuant To Order No. 3, Case 337-TA-1356, Exhibit 2017, (26 pages).
IPR2024-00463, *Jeisys v. Serendia*; Order No. 6 Adopted Procedural Schedule, Case 337-TA-1356, Exhibit 2018, (12 pages).
IPR2024-00463, *Jeisys v. Serendia*; Respondents' Joint Reply Post-Hearing Brief, Case 337-TA-1356, Exhibit 2019, (6 pages).
IPR2024-00463, *Jeisys v. Serendia*; Jeisys and Cynosure's Response to the Complaint and Notice of Investigation, Case 337-TA-1356, Exhibit 2021, (68 pages).
IPR2024-00463, *Jeisys v. Serendia*; Letter from Keith K. Im to Cynosure dated Nov. 29, 2021, Exhibit 2023, (2 pages).
IPR2024-00463, *Jeisys v. Serendia*; Order No. 33 Granting Parties' Joint Motion to Amend the Amended Procedural Schedule dated Oct. 19, 2023, Case 337-TA-1356, Exhibit 2024, (5 pages).
IPR2024-00463, *Jeisys v. Serendia*; Brochure Sylfirm X Dual Wave RF Microneedling System, Exhibit 2037, (16 pages).
IPR2024-00463, *Jeisys v. Serendia*; Respondents' Notice of Prior Art; Case 337-TA-1356, Exhibit 2053, (11 page).
IPR2024-00463, *Jeisys v. Serendia*; Sylfirm X Revolutionizes Clinical Applications of RF Microneedling dated May/Jun. 2022, Exhibit 2066, (3 pages).
IPR2024-00463, *Jeisys v. Serendia*; World-Class Product of Korea 2020 Certificate to ViOL (Dec. 9, 2020); Exhibit 2067, (1 page).
IPR2024-00463, *Jeisys v. Serendia*; Vincent A. Thomas CV; Exhibit 2070, (17 pages).
IPR2024-00463, *Jeisys v. Serendia*; ViOL, Sylfirm X User Manual; Exhibit 2083, (43 pages).
IPR2024-00463, *Jeisys v. Serendia*; Sylfirm X Product Photographs; Exhibit 2086, (11 pages).
IPR2024-00463, *Jeisys v. Serendia*; Sylfirm X Introduction Video 1.mp4, "New X Tips"; Exhibit 2097.
IPR2024-00463, *Jeisys v. Serendia*; Transcript of Sylfirm X Introduction Video 1; Exhibit 2098, (1 page).
IPR2024-00463, *Jeisys v. Serendia*; Deposition Transcript of Peter Crosby taken Sep. 4, 2023, Case 337-TA-1356, Exhibit 2103, (2 pages).
IPR2024-00463, *Jeisys v. Serendia*; Deposition Transcript of Peter Crosby taken Sep. 5, 2023, Case 337-TA-1356, Exhibit 2104, (2 pages).
IPR2024-00463, *Jeisys v. Serendia*; U.S. Patent Application Publication No. 20020120260 A1, Exhibit 2108, (67 pages).
IPR2024-00463, *Jeisys v. Serendia*; Certified English translation of Korean Registered Patent Publication No. KR10-0852500, Exhibit 2110, (11 pages).
IPR2024-00463, *Jeisys v. Serendia*; Respondents' Amended Notice of Prior Art, Case 337-TA-1356, Exhibit 2111, (11 pages).
IPR2024-00463, *Jeisys v. Serendia*; USPTO File History for U.S. Pat. No. 9,320,536, Exhibit 2114, (362 pages).
IPR2024-00463, *Jeisys v. Serendia*; U.S. Pat. No. 6,890,319 B1, Exhibit 2115, (18 pages).
IPR2024-00463, *Jeisys v. Serendia*; U.S. Pat. No. 6,277,116 B1, Exhibit 2119, (22 pages).
IPR2024-00463, *Jeisys v. Serendia*; U.S. Patent Application Publication No. 20020120261 A1, Exhibit 2120, (62 pages).
IPR2024-00463, *Jeisys v. Serendia*; Cartessa Aesthetics, Innovation in RF Microneedling: A closer look at VirtueRF, Jun. 2021, Exhibit 2122, (4 pages).
IPR2024-00463, *Jeisys v. Serendia*; Woloszko Hearing Transcript dated Nov. 7, 2023, Case 337-TA-1356, Exhibit 2125, (69 pages).
IPR2024-00463, *Jeisys v. Serendia*; Crosby Hearing Transcript dated Dec. 12, 2023, Case 337-TA-1356, Exhibit 2126, (31 pages).
IPR2024-00463, *Jeisys v. Serendia*; Sylfirm X—Product Inspection Report, Appendix 17, Case 337-TA-1356, Exhibit 2127, (11 pages).
IPR2024-00463, *Jeisys v. Serendia*; Deposition transcript of Jongju Na dated Jul. 25, 2023, Case 337-TA-1356, Exhibit 2128, (5 pages).
IPR2024-00463, *Jeisys v. Serendia*; Sylfirm X Product Photographs, Exhibit 2130, (4 pages).
IPR2024-00463, *Jeisys v. Serendia*; U.S. Patent Application Publication No. 20060036210 A1, Exhibit 2132, (69 pages).
IPR2024-00463, *Jeisys v. Serendia*; Peter Crosby CV, Exhibit 2136, (8 pages).
IPR2024-00463, *Jeisys v. Serendia*; Appendix 7—U.S. Pat. No. 10,869,812 Patent Summary Invalidity Claim Chart, Exhibit 2139, (7 pages).
IPR2024-00463, Declaration of Peter Crosby in Support Of Patent Owner's Preliminary Response, (*Jeisys Medical Inc. v. Serendia, LLC*; U.S. Pat. No. 10,869,812), Exhibit 2140 (69 pages).
IPR2024-00463, Declaration of Vince Thomas in Support Of Patent Owner's Preliminary Response, (*Jeisys Medical Inc. v. Serendia, LLC*; U.S. Pat. No. 10,869,812), Exhibit 2141 (8 pages).
IPR2024-00463, *Jeisys v. Serendia*; U.S. Patent Application Publication No. 20040058882 A1, Exhibit 2142, (26 pages).
IPR2024-00463, *Jeisys v. Serendia*; U.S. Patent Application Publication No. 20080091182 A1, Exhibit 2143, (35 pages).
IPR2024-00463, *Jeisys v. Serendia*; USPTO Statutory Disclaimer dated May 13, 2024, U.S. Appl. No. 15/724,261, Exhibit 2144, (6 pages).
IPR2024-00383, Patent Owner's Preliminary Response (*Jeisys Medical Inc. and Ilooda Co., Ltd. v. Serendia, LLC*; U.S. Pat. No. 9,775,774), Apr. 23, 2024 (81 pages).
IPR2024-00383, Patent Owner Motion to Seal (*Jeisys Medical Inc. and Ilooda Co., Ltd. v. Serendia, LLC*; U.S. Pat. No. 9,775,774), Apr. 23, 2024 (10 pages).
IPR2024-00383, *Jeisys v. Serendia*; Complainant's Jul. 24, 2023 Supplemental Validity Contentions, Case 337-TA-1356, Exhibit 2003, (425 pages).
IPR2024-00383, *Jeisys v. Serendia*; Expert Report of Jean Woloszko, Case 337-TA-1356, Exhibit 2004, (684 pages).
IPR2024-00383, *Jeisys v. Serendia*; Deposition transcript of Jean Woloszko taken Sep. 14, 2023, Case 337-TA-1356, Exhibit 2007, (2 pages).
IPR2024-00383, *Jeisys v. Serendia*; Deposition transcript of Jean Woloszko taken Sep. 15, 2023, Case 337-TA-1356, Exhibit 2008, (2 pages).
IPR2024-00383, *Jeisys v. Serendia*; Complainant's Public Interest Statement & Complaint of Serendia, Case 337-TA-_, Exhibit 2016, (74 pages).
IPR2024-00383, *Jeisys v. Serendia*; The Parties' Proposed Procedural Schedule and Notice of Proceedings and State and Federal Litigation Pursuant To Order No. 3, Case 337-TA-1356, Exhibit 2017, (26 pages).
IPR2024-00383, *Jeisys v. Serendia*; Order No. 6 Adopted Procedural Schedule, Case 337-TA-1356, Exhibit 2018, (12 pages).
IPR2024-00383, *Jeisys v. Serendia*; Respondents' Joint Reply Post-Hearing Brief, Case 337-TA-1356, Exhibit 2019, (6 pages).
IPR2024-00383, *Jeisys v. Serendia*; Response of Ilooda to the Complaint and Notice of Investigation, Case 337-TA-1356, Exhibit 2020, (88 pages).

(56) References Cited

OTHER PUBLICATIONS

IPR2024-00383, *Jeisys* v. *Serendia*; Jeisys and Cynosure's Response to the Complaint and Notice of Investigation, Case 337-TA-1356, Exhibit 2021, (68 pages).
IPR2024-00383, *Jeisys* v. *Serendia*; Letter from Merle W. Richman to Cutera dated Mar. 20, 2018, Exhibit 2022, (1 page).
IPR2024-00383, *Jeisys* v. *Serendia*; Letter from Keith K. Im to Cynosure dated Nov. 29, 2021, Exhibit 2023, (2 pages).
IPR2024-00383, *Jeisys* v. *Serendia*; Order No. 33 Granting Parties' Joint Motion to Amend the Amended Procedural Schedule dated Oct. 19, 2023, Case 337-TA-1356, Exhibit 2024, (5 pages).
IPR2024-00383, *Jeisys* v. *Serendia*; Brochure Sylfirm X Dual Wave RF Microneedling System, Exhibit 2037, (16 pages).
IPR2024-00383, *Jeisys* v. *Serendia*; Respondents' Notice of Prior Art; Case 337-TA-1356, Exhibit 2053, (11 page).
IPR2024-00383, *Jeisys* v. *Serendia*; Sylfirm X Revolutionizes Clinical Applications of RF Microneedling dated May/Jun. 2022, Exhibit 2066, (3 pages).
IPR2024-00383, *Jeisys* v. *Serendia*; World-Class Product of Korea 2020 Certificate to ViOL (Dec. 9, 2020); Exhibit 2067, (1 page).
IPR2024-00383, *Jeisys* v. *Serendia*; Vincent A. Thomas CV; Exhibit 2070, (17 pages).
IPR2024-00383, *Jeisys* v. *Serendia*; ViOL, Sylfirm X User Manual; Exhibit 2083, (43 pages).
IPR2024-00383, *Jeisys* v. *Serendia*; Sylfirm X Product Photographs; Exhibit 2086, (11 pages).
IPR2024-00383, *Jeisys* v. *Serendia*; Sylfirm X Introduction Video 1.mp4, "New X Tips"; Exhibit 2097.
IPR2024-00383, *Jeisys* v. *Serendia*; Transcript of Sylfirm X Introduction Video 1; Exhibit 2098, (1 page).
IPR2024-00383, *Jeisys* v. *Serendia*; Deposition Transcript of Peter Crosby taken Sep. 4, 2023, Case 337-TA-1356, Exhibit 2103, (2 pages).
IPR2024-00383, *Jeisys* v. *Serendia*; Deposition Transcript of Peter Crosby taken Sep. 5, 2023, Case 337-TA-1356, Exhibit 2104, (2 pages).
IPR2024-00383, *Jeisys* v. *Serendia*; USPTO Statutory Disclaimer dated Apr. 19, 2024, U.S. Appl. No. 15/096,686, Exhibit 2105, (11 pages).
IPR2024-00383, *Jeisys* v. *Serendia*; U.S. Patent Application Publication No. 20020120260 A1, Exhibit 2108, (67 pages).
IPR2024-00383, *Jeisys* v. *Serendia*; U.S. Patent Application Publication No. 20030130711 A1, Exhibit 2109, (54 pages).
IPR2024-00383, *Jeisys* v. *Serendia*; Certified English translation of Korean Registered Patent Publication No. KR10-0852500, Exhibit 2110, (11 pages).
IPR2024-00383, *Jeisys* v. *Serendia*; Respondents' Amended Notice of Prior Art, Case 337-TA-1356, Exhibit 2111, (11 pages).
IPR2024-00383, *Jeisys* v. *Serendia*; Appendix 6—Summary Invalidity Claim Chart; U.S. Pat. No. 9,775,774, Case 337-TA-1356, Exhibit 2113, (1 page).
IPR2024-00383, *Jeisys* v. *Serendia*; USPTO File History for U.S. Pat. No. 9,320,536, Exhibit 2114, (362 pages).
IPR2024-00383, *Jeisys* v. *Serendia*; U.S. Pat. No. 6,890,319 B1, Exhibit 2115, (18 pages).
IPR2024-00383, *Jeisys* v. *Serendia*; U.S. Pat. No. 10,869,812 B2, Exhibit 2116, (32 pages).
IPR2024-00383, *Jeisys* v. *Serendia*; U.S. Pat. No. 8,540,705 B2, Exhibit 2117, (51 pages).
IPR2024-00383, *Jeisys* v. *Serendia*; USPTO File History for U.S. Pat. No. 10869812, Exhibit 2118, (733 pages).
IPR2024-00383, *Jeisys* v. *Serendia*; U.S. Pat. No. 6,277,116 B1, Exhibit 2119, (22 pages).
IPR2024-00383, *Jeisys* v. *Serendia*; U.S. Patent Application Publication No. 20020120261 A1, Exhibit 2120, (62 pages).
IPR2024-00383, *Jeisys* v. *Serendia*; Cartessa Aesthetics, Innovation in RF Microneedling: A closer look at VirtueRF, Jun. 2021, Exhibit 2122, (4 pages).
IPR2024-00383, Declaration of Peter Crosby in Support Of Patent Owner's Preliminary Response, (*Jeisys Medical Inc. and Ilooda Co., Ltd.* v. *Serendia, LLC*; U.S. Pat. No. 9,775,774), Exhibit 2123 (63 pages).
IPR2024-00383, Declaration of Vince Thomas in Support Of Patent Owner's Preliminary Response, (*Jeisys Medical Inc. and Ilooda Co., Ltd.* v. *Serendia, LLC*; U.S. Pat. No. 9,775,774), Exhibit 2124 (8 pages).
IPR2024-00383, *Jeisys* v. *Serendia*; Woloszko Hearing Transcript dated Nov. 7, 2023, Case 337-TA-1356, Exhibit 2125, (69 pages).
IPR2024-00383, *Jeisys* v. *Serendia*; Crosby Hearing Transcript dated Dec. 12, 2023, Case 337-TA-1356, Exhibit 2126, (31 pages).
IPR2024-00383, *Jeisys* v. *Serendia*; Crosby Opening Expert Report—Appendix 17, Exhibit 2127, (11 pages).
IPR2024-00383, *Jeisys* v. *Serendia*; Deposition transcript of Jongju Na dated Jul. 25, 2023, Case 337-TA-1356, Exhibit 2128, (5 pages).
IPR2024-00383, *Jeisys* v. *Serendia*; Sylfirm X Product Photographs, Exhibit 2130, (4 pages).
IPR2024-00383, *Jeisys* v. *Serendia*; Peter Crosby CV, Exhibit 2136, (8 pages).

\* cited by examiner

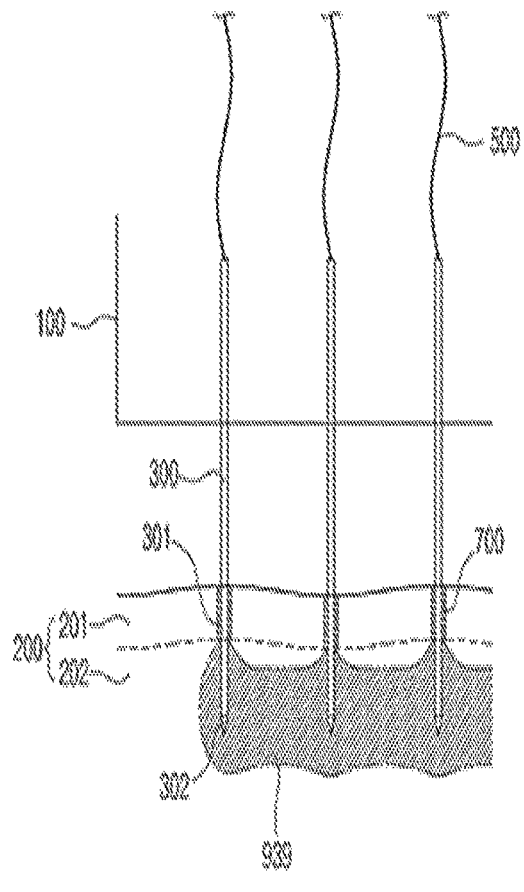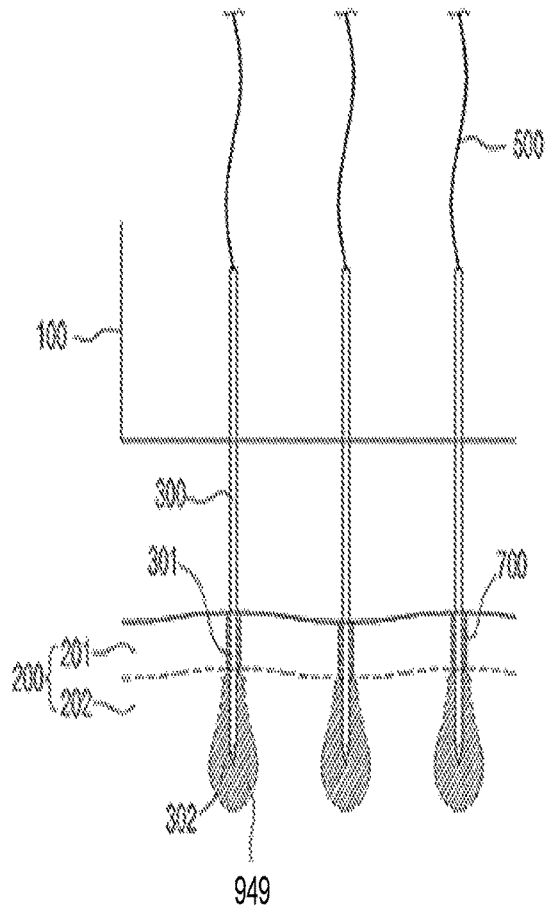
FIGURE 9A
FIGURE 9B

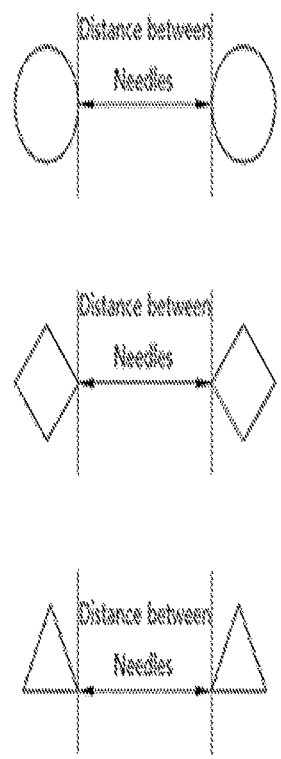
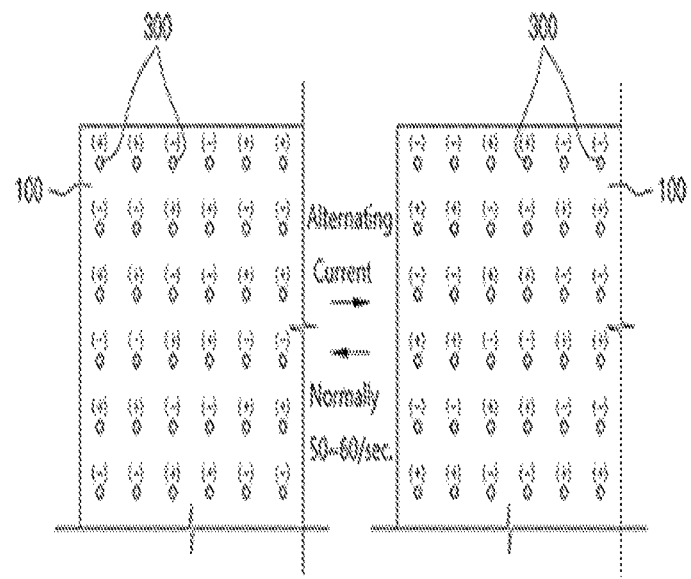
FIGURE 10
FIGURE 11

ELECTRICALLY BASED MEDICAL TREATMENT DEVICE AND METHOD

CROSS REFERENCE TO RELATED APPLICATIONS

The present application is a continuation of U.S. patent application Ser. No. 17/686,405, entitled "ELECTRICALLY BASED MEDICAL TREATMENT DEVICE AND METHOD", filed on Mar. 3, 2022, which is a continuation of U.S. patent application Ser. No. 17/061,523, entitled "ELECTRICALLY BASED MEDICAL TREATMENT DEVICE AND METHOD", filed on Oct. 1, 2020, now U.S. Pat. No. 11,406,444, which is a continuation of U.S. patent application Ser. No. 16/111,616, entitled "ELECTRICALLY BASED MEDICAL TREATMENT DEVICE AND METHOD", filed on Aug. 24, 2018, now U.S. Pat. No. 10,799,286, which is a continuation of U.S. patent application Ser. No. 15/202,511, entitled "ELECTRICALLY BASED MEDICAL TREATMENT DEVICE AND METHOD", filed on Jul. 5, 2016, now U.S. Pat. No. 10,058,379, which is a continuation of U.S. patent application Ser. No. 14/006,930, entitled "SKIN TREATMENT APPARATUS AND METHOD", filed on: Nov. 29, 2013, now U.S. Pat. No. 9,480,836, which is a Rule 371 national stage entry of PCT Application Number PCT/KR2012/004695, entitled "APPARATUS AND METHOD FOR IMPROVING SKIN USING A NA-EFFECT OR NA PLUS-EFFECT", filed on Jun. 14, 2012, which claims the benefit of priority to Republic of Korea Application Number 10-2011-0057691, entitled "APPARATUS AND METHOD FOR IMPROVING SKIN USING A NA-EFFECT OR NA PLUS-EFFECT," filed on Jun. 14, 2011, and Republic of Korea Application Number 10-2011-0057692, entitled "APPARATUS AND METHOD FOR IMPROVING SKIN USING A NA-EFFECT OR NA PLUS-EFFECT," filed on Jun. 14, 2011, the entirety of each is incorporated by reference.

TECHNICAL FIELD

This invention is for medical treatment including skin treatment using electrical energy, especially with the primary purpose for skin treatment for aesthetics, and in some cases, can be used as a direct instrument or supplement for skin cosmetic surgery. In detail, this invention is to provide skin treatment using method and device using high frequency, which minimizes skin aging by directly stimulating dermis between epidermis and subcutaneous layer.

BACKGROUND INFORMATION

Generally, skin is the largest protective organ that covers the entire body and maintains homeostasis on surface of the body with three layers consisting of epidermis, dermis, and subcutaneous layer.

Dermis is the layer beneath epidermis, directly connected to a basal layer. Skin is made up of dermis that includes protein, glycoside, glycosaminoglycan, mineral, and inorganic salt in gelatinous form. In Dermis there are two layers: papillary and reticular layer. The Papillary layer includes of capillaries and lymphatics. Capillaries provide nutrition to skin and circulate blood. Lymphatics carry lymph. The Reticular layer includes collagen, elastin and a substrate. Collagen is a fiber related to skin wrinkle, elastin is an elastic fiber that gives elasticity to skin, and the substrate is mostly made of water. The Subcutaneous layer lies below dermis, contains plenty of fat, and attaches the skin to underlying muscle and bone.

One of the most popular treatments to prevent skin aging is massaging with a nutritious substance. Although this type of skin treatment provides nutrition to epidermis and may make skin glow, it does not last for long and rarely shows improvement instantaneously.

Another treatment uses a syringe to inject serum into the skin, but this treatment method is costly and causes side effects based on individual skin characteristics that result adversely affecting the skin.

A further treatment delivers high frequency energy indirectly to the dermis via the skin surface. Even with a high energy signal, this treatment does not effectively transmit high frequency energy to the dermis via the skin surface. Also, this treatment is costly because patients may need to receive multiple treatments to obtain measurable results.

Korean patent 2000-0058346 describes a device to reduce skin wrinkles by verifying wrinkle thickness, length and shape and setting pulse, time, elevation current and wattage to magnify the cell tissue. Via a hand piece, the needle length may be selected based on the length and depth of wrinkle to be reduced. The device uses a single needle that may not be sufficient for treatment. Korean patent 10-2009-23494 describes employing high frequency to treat skin. In detail, it attempts to revitalize cell tissue and maintain elasticity in skin, and minimizing skin aging by directly delivering high frequency energy into skin dermis (between epidermis and subcutaneous layer). The skin treatment device includes a pair of electrodes in a main body that deliver high frequency energy into the dermis reticular layer. This treatment method may include side effects, not limited to burning both epidermis and dermis between the needles, which may form a scar. Another problem of the treatment is maintaining finite control.

To limit epidermis burning the needles may be insulated except at the tip portion. Insulated needles may cause bigger penetration marks, pain and possible allergic reactions in patients. The needle insulation may also fail or come off due to repeated penetration resulting in heating of unintended areas. In addition, the device may generate a high temperature around needle tip and increase the possibility of dermis burning since the needle surface area is reduced by the insulation.

Another device uses a monopole configuration with a single electrode and a ground on another body location. Such a configuration may require large voltages to conduct enough energy to generate desired heat. The high voltage conduction may impact unintended body parts including the heart.

SUMMARY OF THE INVENTION

The present invention is a method and apparatus that provides electric stimulation directly to a body region including the dermis via needles. This method revitalizes and regenerates the body region including collagen by wounding the dermis.

As noted, dermis is composed of protein called collagen. Collagen is a triple helical structure including fibroblasts and polypeptides. When collagen tissue is heated, a physical transformation of protein matrix part occurs at a shrinkage temperature. Soft tissue remodeling is a transformation and phenomenon that happens at cellular and molecular level when the triple helical binding is disassembled by partial denaturalization of collagen due to shrinkage caused by artificial heat, resulting in destruction of molecular bindings of the protein matrix. When the cell shrinkage occurs, collagen is present on lower cell part and supports the protein matrix within the resulting tightened soft tissue. The initial deposition and subsequent remodeling of scar matrix may offer a way to aesthetically modify the shape and consistency of soft tissue. Soft tissue remodeling may appear immediately compared to the shrinkage that results from the movement of fibroblast cell or natural healing. Ultimately, a treatment for improving skin or reducing wrinkles may apply various energy sources to selected areas to solidify the tissue.

When energy is applied to dermis, the effect on the dermis may differ based on the amount of energy applied and the effect is generally divided into three phenomena: carbonization, vaporization, and coagulation. The present invention improves skin condition by primarily using coagulation. The three phenomena: carbonization, vaporization, and coagulation can also be expressed as "to burn", "to apply heat", "to raise temperature", although none of these phrases are exact. The invention may configured "to raise temperature" by applying energy to achieve coagulation.

In the present invention the term "to raise temperature" is used synonymously with "applying energy to achieve coagulation" where applying electrically energy to the body region may effectively raise the body region temperature. The present invention was created to resolve above mentioned problems.

An embodiment of the present invention includes a skin improvement device and method is to resolve above mentioned problems. The present invention is a byproduct of newly discovered effects. A first embodiment is shown in FIG. 5. Other embodiments are shown FIGS. 7, 8 and 9B. Several embodiments of the present invention may employ non insulated needles, especially in areas where the needles come in contact with dermis.

In an embodiment heated areas may be different from other electrodes employing systems. In the present invention the temperature may be raised and the heat may be concentrated at an area in dermis by the needle(s) to cause coagulation. The heat generated by the present invention may minimally affect the adjacent epidermis area. Also, the heated area around the needle end tips may be oval or tear shaped as shown in FIG. 5. In an embodiment heat may not be concentrated between needles. In an embodiment, the heated area may be around each needle.

In an embodiment, the temperature is raised about the tip of each needle, not between needles. The method of the present invention may control electrical factors or distance between needles to control the energy field applied between needles. A method of the present invention may enable users to control the number of treatments in target areas by controlling the dissipated energy in needles.

In an embodiment, higher temperatures may be concentrated in dermis, not epidermis, enabling the use of non-insulated needles. The present invention may have a definite advantage over the systems that employ insulated needles. An embodiment of the present invention may not require insulated needles except for special cases. In some treatment cases, an embodiment of the present invention may employ insulating needles in an area where it comes in contact with epidermis, but insulation is not required.

An embodiment of the present invention may employ bipolar needles, alternating current (AC) signals, and high frequency signals. In an embodiment the distance between electrodes or needles may be important because if the distance between electrodes is too close, heated areas about each needle tip may overlap. However, in another embodiment a close distance between needles may not be critical.

As noted the present invention may use non-insulated needles. Other embodiments may use insulated needles but may, decrease the effectiveness of treatments employing insulated needles. Because the needles are stimulated via opposite polarity, AC signals, each needle may independently form an energy field about its tip, where the energy field may raise the temperature of adjacent tissue as a function of the tissue anatomy. Thus, each needle of the plurality of needles may as if independently stimulated and grounded from the other of the plurality of needles.

In an embodiment employed needles polarities may form a net or checked shape when viewed from needle tips. In an embodiment, four or more needles may be employed. In an embodiment where the needles form a rectangular plane, four or more needles may be used on each quadrant.

In an embodiment adjacent or neighboring needles may be configured to have opposite polarities (+) and (−) such as shown in FIG. 6.

Embodiments of the present invention may resolve problems of existing technologies.

A serious side effect of some existing technologies, systems, or treatments is overheating or burning of both dermis and epidermis located between needles, which may cause permanent skin damage. An embodiment of the present invention may prevent or limit overheating between needles.

As noted embodiments of the present invention may generate an oval or tear shaped, heated area in dermis about each needle tip. Embodiments of the present invention may minimally raise temperature epidermis as shown in FIG. 5. Method of the present invention may control electrical factors or distance between needles to control temperature between needles.

Existing technology may create scars created in overheated or burned epidermis. Further damage may be caused by trying to treat the scars. Embodiment of the present invention attempt to prevent overheating or burning of epidermis. Embodiments of the present invention may not use insulation as insulation may reduce effectiveness. Further, insulted needles may need to be thicker, causing more patient pain and leaving insertion marks. Further insulation deposited from needles may cause serious side effects.

BRIEF EXPLANATIONS OF THE DRAWINGS

FIG. 9A is a simplified diagram of a treatment architecture according to an embodiment of the present invention with overlapping or intersecting energy fields.

FIG. 9B is a simplified diagram of a treatment architecture according to an embodiment of the present invention with non-overlapping or non-intersecting energy fields.

FIG. 10 is a simplified diagram of a treatment architecture illustrating a polarity change of needles according to according to an embodiment of the present invention.

FIG. 11 is a simplified diagram illustrating the distance between two needles according to various embodiments of the present invention.

DETAILED DESCRIPTION

The following is to explain an embodiment of this invention in detail.

TABLE OF REFERENCES

Number Description
    100: fixture holding needles
    200: skin
    201: epidermis
    202: dermis
    300: pin/needle/electrode
    301: needle area penetrating skin
    302: end of needle area penetrating into dermis
    400: patient's hand receiving treatment using monopole method
    500, 600: electrical wire
    700: insulated area of needle
    901: area where the temperature is raised when using monopole electrode
    902: area where the temperature is raised when using non-insulated bipolar needles
    903: area where the temperature is raised using insulated needles with non-insulated tips
    909, 919, 929: area where the temperature is raised using non-insulated needles.
    939, 949: area where the temperature is raised using partially insulated needles in epidermis.

Figure 1:
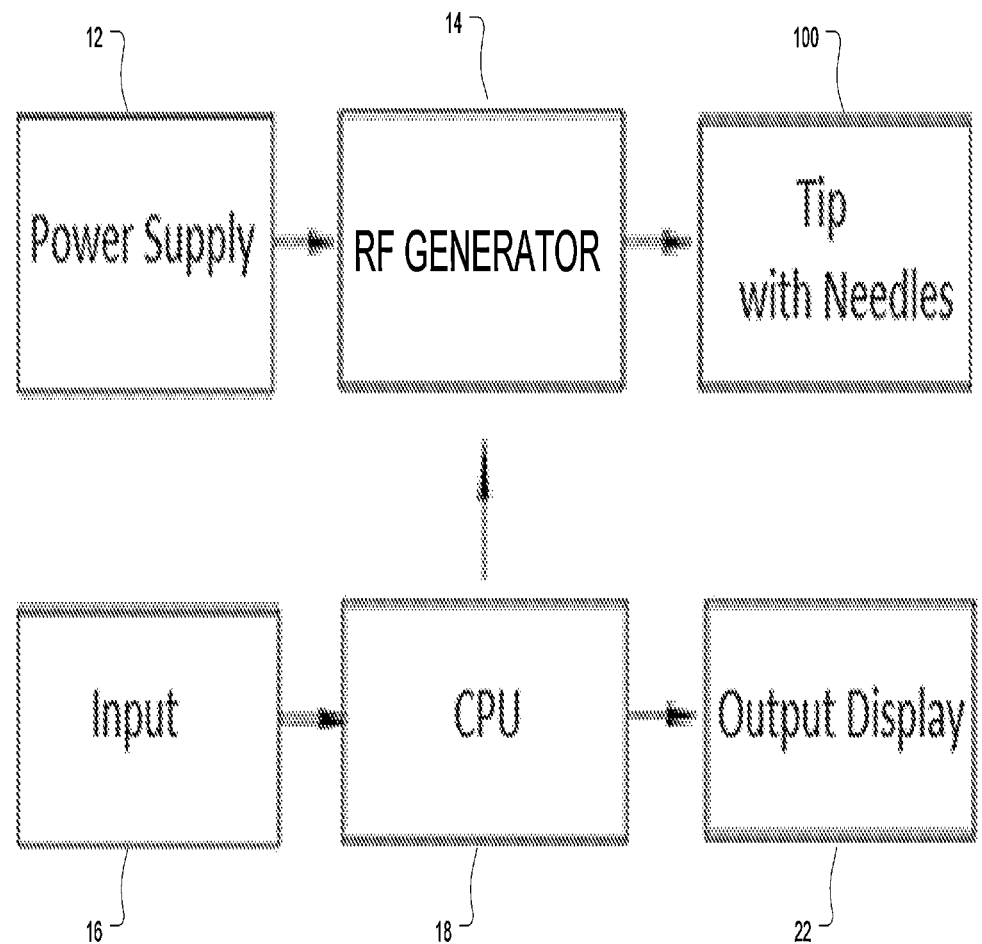
FIG. 1 is a block diagram of an apparatus according to an embodiment of the present invention.

This invention pursues multiple embodiments, where the embodiments may be related. Technological components of various embodiments may be similar. Embodiments may vary based on voltage, current, application time, needle thickness, resistance, AC frequency, high frequency, conductivity, and needle penetration depth. FIG. 1 is a block diagram a system 10 according to various embodiments. As shown in FIG. 1, the system 10 may include a power supply 12, an RF generator 14, a user input 16, a central processing unit 18, a user detectable output display 22, and a device (tip) 100 with a plurality of needles 300. The power supply 12 may provide required energy to the radio frequency (RF) generator 14. A user input device 16 may enable a user to set several parameters that control the energy field 909 generated about needles 300 in the tip or device 100 including the voltage, current, and frequency applied to the needles 300, the on time and off time of the RF signal during the cycles, the deployed depth of the needles (to treat a body region including epidermis, dermis, and subcutaneous sections of skin). The input device may be any device enabling a user to select various parameters including a keyboard, touch screen, or other user input device.

The system 10 output device 22 may be any user detectable output device including a user readable screen, light(s), and audio generation devices. The CPU 18 may receive the user selected parameters for the device 100 operation and control the operation of the RF generator 14 based on the user selected parameters. The CPU 18 may also provide a signal to generate an output signal displayable by the output device 22, the output signal indicating the operational state of the system 100 according to various embodiments. The RF generator 14 may generate signal or signal(s) having a desired voltage, current, energy, resistance, RF frequency, on cycle, off cycle, and other parameters according to various embodiments.

Figure 2:
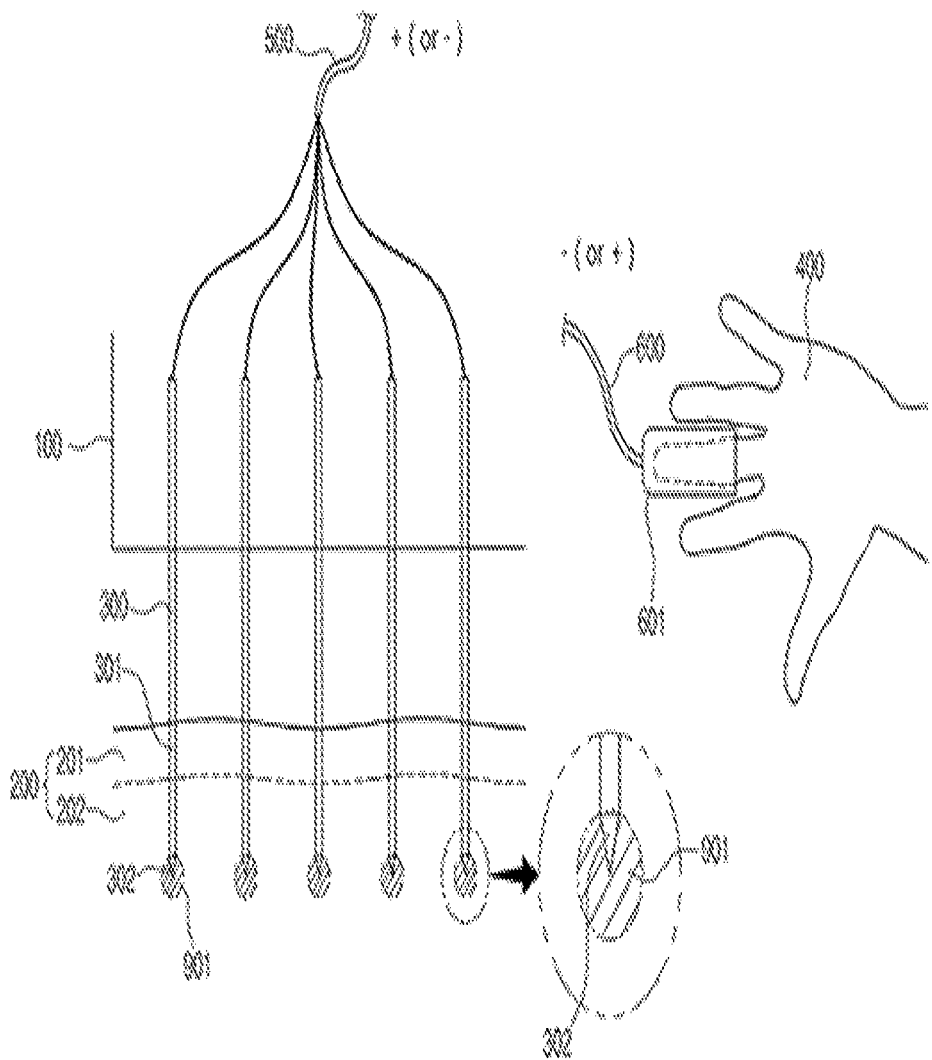
FIG. 2 is a simplified diagram of treatment architecture using monopole needles according to an embodiment of the present invention.
Figure 3:
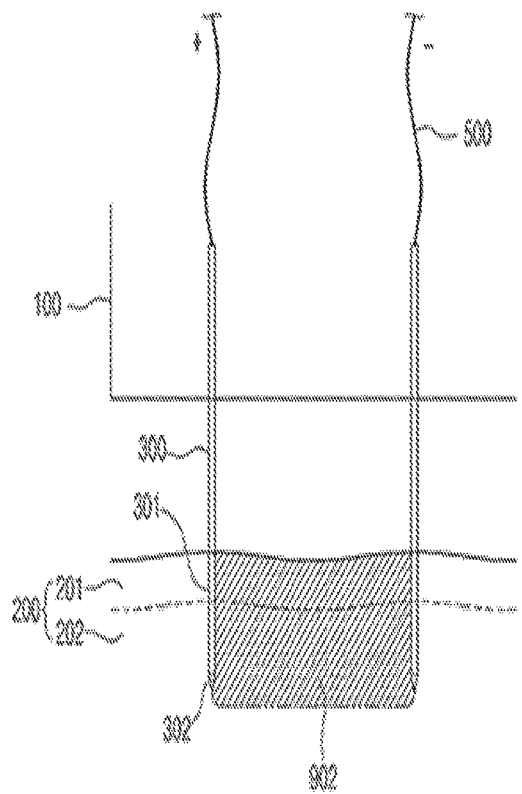
FIG. 3 is a simplified diagram of treatment architecture using non-insulated bipolar needles according to an embodiment of the present invention.
Figure 4:
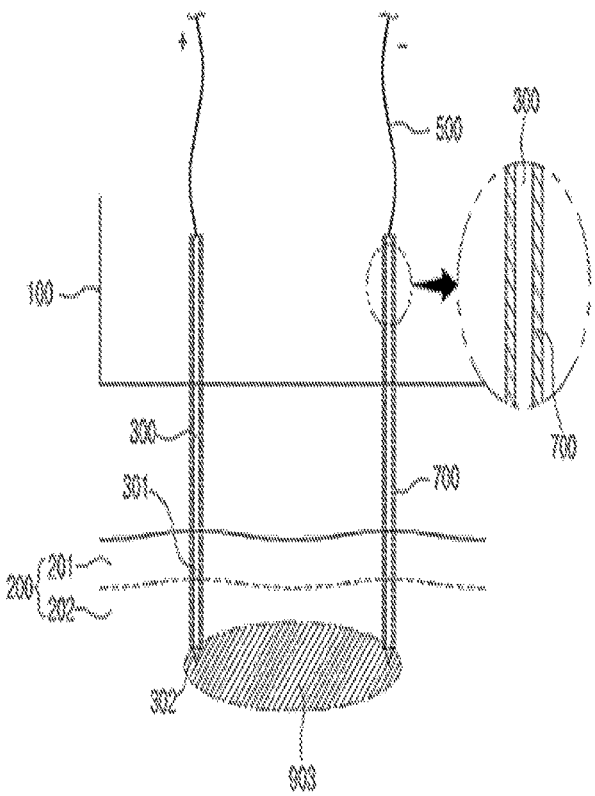
FIG. 4 is a simplified diagram of treatment architecture using bipolar needles that are insulated except at the needle tip according to an embodiment of the present invention.
Figure 5:
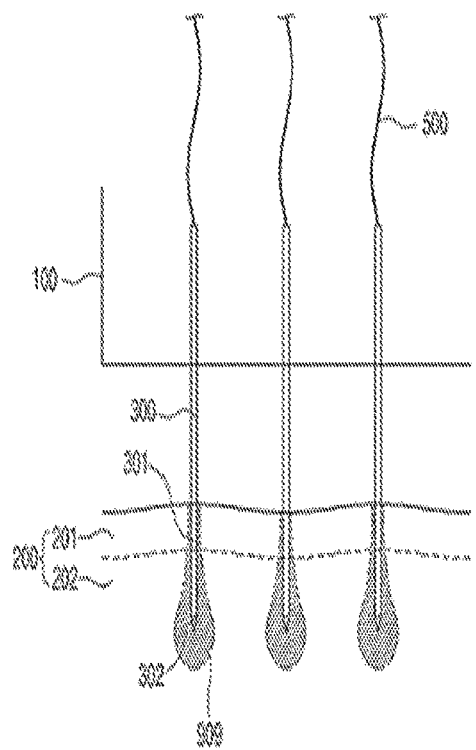
FIG. 5 is a simplified diagram of treatment architecture using non insulated needles according to an embodiment of the present invention.
Figure 7:
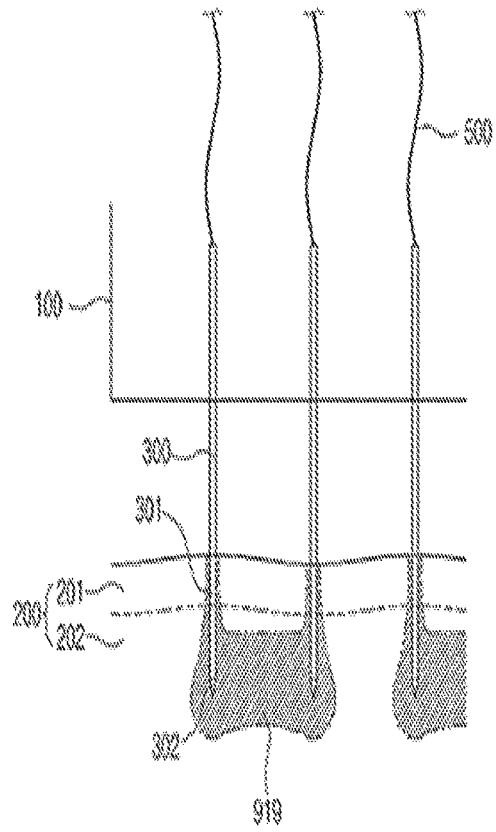
FIG. 7 is a simplified diagram of a treatment architecture according to an embodiment of the present invention.
Figure 8:
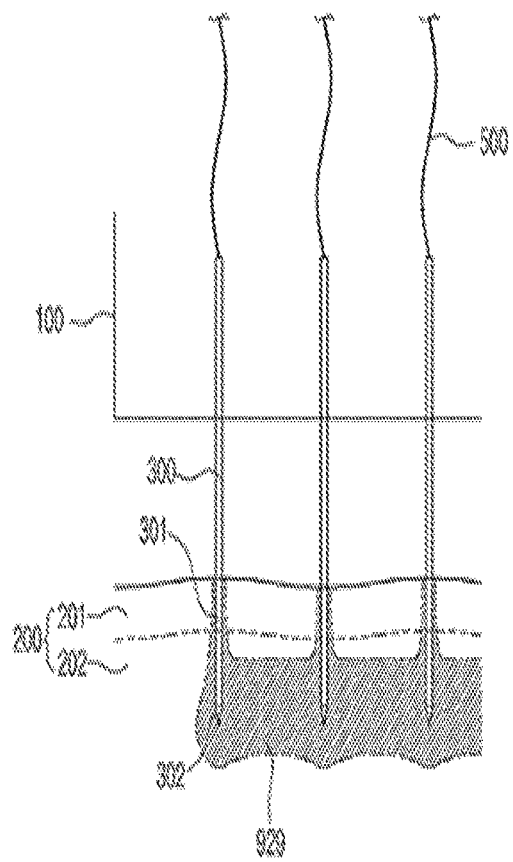
FIG. 8 is a simplified diagram of a treatment architecture according to an embodiment of the present invention.

Some embodiments may employ bipolar needles, AC and high frequency signals. The distance between needles may vary for different embodiments. In an embodiment needles 301 (FIG. 2) may not be located close proximity because if the distance between electrodes or needles is too close, the energy field and the heated area generated by the applied energy field about each needle may be connected or intersect. In another embodiment the energy fields (generating heated areas in dermis) may be expanded and connected in dermis, but not in epidermis as shown in FIGS. 7 and 8.

In an embodiment, alternating current (AC) is the current that changes magnitude and direction periodically and may be a known waveform including a sine wave, triangular, or square wave. AC has characteristics that differ from direct current (DC), which flows in one direction and has a constant polarity. On-grid AC provided by power companies commonly alternates polarity about either at 50 Hz or 60 Hz worldwide.

In an embodiment, actuating needles with AC may be a factor to generate a desired effect or energy field about the each needle. In an embodiment, the AC frequency may be be hundreds of Hz to achieve the desired effect. For high frequency AC sources, the distance between needles may be decreased to compensate for the effect of the high frequency AC source. Low frequency AC sources may affect operation in an embodiment. AC sources having a frequency of 20 Hz or higher may not create a desired operation in an embodiment by controlling other factors. Those control factors are discussed below. In an embodiment, high frequency AC sources may be employed versus low and medium frequencies, and ultrasonic waves or sources.

In an embodiment the AC source may have a frequency above 0.5 MHz and about 2 MHz in another embodiment. Other embodiments may employ an AC signal having a frequency from 0.5 to 10 MHz, 1 to 4 MHz, and 1.5-2.5 MHz where the AC frequency selected range may vary depending on other operating factors that affect desired performance.

During electricity conductivity tests for dry skin and wet skin with AC signals having frequencies of 2 MHz and 1 MHz, it was noted that dry skin had a conductance of about 0.037102 at 2 MHz and about 0.013237 at 1 MHz and wet skin had a conductance of about 0.26649 at 2 MHz and about 0.2214 at 1 MHz. Consequently, RF energy flow or conductance may be smoother or less resistive when applied to wet skin at 2 MHz. Based on the lower conductance the probability for sparking for energy applied at 1 MHz (ignoring other variables) may be three times higher than 2 MHz energy.

In an embodiment a high frequency applied current may create an energy field closer to an electrode or needle than an equivalent energy low frequency current.

For example, when AC signals having a frequency below 0.5 MHz are applied to a needle or electrode the area impacted by the resultant, broad energy field may cause scaring in adjacent epidermis due to overheating regardless of electrode or needle spacing. Accordingly, for areas where a precise treatment is required such as around eyelid, the source frequency may be selected to prevent a broad energy field formation about the needles or electrodes to prevent a harmful impact on an eye. It is noted that when the source energy frequency is 10 MHz or above, the energy field formed about the needles or electrodes may be too narrow and thereby increase treatment time to achieve a desired therapy In various embodiments, achieving a desired therapy may be related to the distance between deployed needles. For example, as the distance between needles decreases the source frequency value may be increased and conversely, as the distance between needles increases, the source frequency value may be decreased to achieve or limit the energy field formation about energized needles or electrodes. In an embodiment, adjacent needles are spaced about 2 mm apart when the needle energizing signal has a frequency of about 2 MHz.

In an embodiment, energized needles may be completely electrically insulated, un-insulated, and only insulated near its tip. Needle insulation may not be necessary fin an embodiment to achieve a desired energy field about the needle, in particular so the temperature is raised about the needle tip and the energy field forms an oval or tear shape in the adjacent dermis while the temperature is minimally raised in the epidermis, as shown in FIGS. 5, 7, 8 and 9B. However, non-electrical insulation coating may not affect energy field formation in about embodiment as shown in FIG. 9B. In an embodiment, needles may be plated with other precious metals or heat-treated to modify needle or electrode conductivity and hardness.

In an embodiment, the needles may not be insulated. In embodiments where at least a portion of the needle is insulated, the segment or area of needle that is configured to contact the dermis may not be insulated. In an embodiment, the entire needle to be energized may be insulated while generating a desired energy field about the needle in the dermis. In an embodiment, a monopole needle insulated except for its tip may be employed to achieve an energy field with a desired shape and temperature. It is important to note that the similarity in energy field shape may have a different effect depending the method applied.

Figure 6:
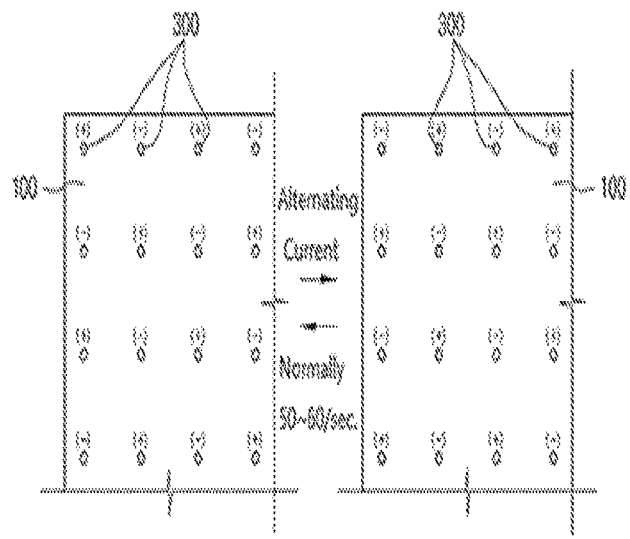
FIG. 6 is a simplified diagram of a treatment architecture illustrating a polarity change of needles according to according to an embodiment of the present invention.

In an embodiment, different needle arrangements may be employed. In one embodiment, neighboring or adjacent needles 300 may be configured to have opposite polarities as shown in FIG. 6. As shown in FIG. 6, a needle configuration 100 may include needles 300 arranged in a rectangular shape where needles on each corner are configured to have a polarity opposite its adjacent or neighboring needles. In an embodiment, different AC signals having opposite polarities may be applied to needles 300 designated (+) and (−). Because of AC signal characteristics, the polarity of each needle may change many times per second (up to 10 MhZ in an embodiment) and cause a needle 300 polarity to change as shown in FIG. 6 at applied AC signal rate. In an embodiment, each needle is configured to have a polarity that is opposite to its closest neighboring needles, polarity shown as in (+) and (−) in FIG. 6 due to the signals applied to the needles 300 via the RF signal generator 14 (FIG. 1).

In an embodiment, a needle 300 cross-section may be configured in a square shape 100 (see FIG. 11). In other embodiments, the needles 300 may be configured in the shape of a rhombus, rectangle, circle, oval, or quadrangle (see FIG. 11). In an embodiment, regardless of shape, the neighboring needles may be configured to have opposite polarities when signals are applied by the RF signal generator 14 (FIG. 1).

In an embodiment, one or more needles 100 may be non-conductive, not energized, or physically removed from particular positions and still produce desired energy fields about the needles in the desired anatomy. In an embodiment, each, closest neighboring needles have opposite polarities, crossing in each direction as in (+) and (−), and a form a square shape 100 having sixteen needles 300.

FIG. 10 is a simplified diagram 100 of another needle 300 arrangement 100 according to various embodiments. In an embodiment, the polarity of needles 300 may be configured to change with every two, adjacent needles to form a pattern of (−) (−) (+) (+). In another embodiment, two or more needles may have the same polarity and then next set has an opposite polarity based on the signals applied to the needles 300. A variety of needle 300 polarity combinations, placements, and needle shapes 100 may be used in designing a device that generates a desired energy field about a needle 300 including the configurations shown in FIG. 6 and FIG. 10.

In an embodiment, a device or needle configuration 100 may have a minimum number of needles is 4. In another embodiment, a device or needle configuration may have a minimum of 9 needles with the polarity arrangement shown in FIG. 6 or FIG. 10.

As noted above other needle arrangements can be configured according to various embodiments where the needles produce a desired energy field about the needle.

In order to generate a desired energy field 909 (FIG. 5), 949 (FIG. 9B) about one or more needle 300 tips 302, an embodiment of the present invention may regulate voltage to be applied to a needle in addition to polarity, pattern, shape, adjacent distance, and frequency. In an embodiment, the voltage level applied to one or more needles 300 may determine or be a factor in setting the distance between needles 300 and ensuring safety of a device including the needles 300. In an embodiment, the voltage applied to skin may be measured.

In an embodiment the meaning of "the applied voltage to skin" may be the actual voltage applied to skin between the surface of a needle and the skin the needle contacts. The actual voltage value as applied to the skin may vary on device resistance, needle resistance and skin resistance at different needle positions. The voltage applied to a needle may be different to the voltage actually applied to the skin due to the skin resistance.

Skin resistance values may vary sub-dermally, but negligibly. It is noted that the applied voltage may be directly related to the amount of energy created at a needle. In an embodiment, the voltage applied to a needle or electrode may not exceed 100V with a recommended operating range between 10 to 60V and about 20 to 40V in a particular embodiment. In an embodiment, voltages above 100V may be applied, but there may cause skin overheating or burning so such voltages may not be recommended for use as the operating voltage for skin treatment. The actual skin voltage and the device operating voltage may be controlled by in an embodiment of the present invention. Given a relatively constant skin resistance, controlling the voltage applied to a needle 300 or group of needles 100 may also control the current flowing in the needle and the skin adjacent to the needle. In particular, the electric current may vary depending on voltage and resistance, but it is possible to compute the value of the electric current when device resistance, needle resistance, and skin resistance values are determined based on the equation:

$$V = I * R$$

A systems resistance may be related to device resistance 100, needle resistance 300, and skin 200 resistance in an embodiment.

In order to generate a desired energy field 909, 949 about one or more needle 300 tips 302, an embodiment of the present invention may regulate the energy duty cycle. In an embodiment a system 100 may take a minimum of 0.02 seconds for high frequency energy to reach its stability so a desired energy field 909, 949 is achieved about a needle 302. If the energy duration or cycle is less than 0.02 seconds, a desired energy field 909, 949 may not be achieved in an embodiment. In an embodiment, the minimum duty cycle was set to be 0.5 seconds or greater. A major advantage of this embodiment is the relatively short energy retention or duty cycle with a longest retention time about 0.8 seconds. In another embodiment the energy retention time or duty cycle may be increased by increasing the distance between needles 300 and lowering the applied voltage. In an embodiment the energy retention time or duty cycle is between 0.05 to 0.8 seconds.

An optimal duty cycle, on time, or retention time or delay between cycles is not intuitive given it is relatively short. In an embodiment an acceptable energy delivery delay may be between 0.1 to 0.4 seconds, with a range from 0.1 to 0.2 seconds in another embodiment. It was discovered that using high frequency and low voltage signals applied to needles 300 having a desired spacing created an energy field that enables effective skin treatment. In an embodiment a desirable delay time may be between 0.1-0.4 seconds and as about 0.1-0.2 seconds in a particular embodiment. Determining the parameters to enable the desired energy field according the present invention required countless trials and errors with insight. After developing the embodiments to form the desired energy field, it is possible to use a short load time in conjunction with a high frequency, low voltage, and alternating current signal.

Some existing systems may apply high voltage signals with an on time greater 0.5 seconds to skin via electrodes versus embodiments of the present invention that generate signals having a shorter on time.

In order to generate a desired energy field 909, 949 about one or more needle 300 tips 302, an embodiment of the present invention may employ needles with particular lengths and thicknesses. Needle thickness may vary with needle distance in an embodiment. In an embodiment a needle should be thick enough and made of a material strong enough to withstand repetitive penetrations into a body region, skin in an embodiment. An embodiment may need to balance thickness with possible patient pain and scars.

In an embodiment, a needle may have a diameter or outer profile of about 0.25 mm and 0.30 mm but is not critical to achieve desired energy fields 909, 949. The needle length may also vary depending on the thickness of the body region (skin in embodiment) to be treated and the type of treatment. In general, epidermis depth may be between 0.2 mm and 1 mm and dermis depth may be between 1 mm and 4 mm (from the skin boundary). In an embodiment a needle may configured to reach at least the top of the dermis, at least 0.2 mm in length in an embodiment and have a maximum length of about 5 mm to reach or penetrate to the dermis center or bottom. To ensure safe use in an embodiment a needle length may enable an ideal treatment depth from 1 mm-5 mm. In an embodiment, a needle total length may vary on the device 100, with a range between 1 mm to 4 mm.

Epidermis consists of stratum corneum, stratum granulosum, stratum spinosum, stratum basale, each with a potentially different resistance level. Epidermis may be treated with a device 100 having needles 300 with a length of about 1 mm. Another device 100 according to various embodiments may employ needles have a length of about 6 mm to treat skin's subcutaneous layer. Accordingly in an embodiment a device 100 may employ a needle that penetrates to a depth between 1 mm to 6 mm.

In order to generate a desired energy field 909, 949 about one or more needle 300 tips 302, an embodiment of the present invention may employ needles having a desired distance and shape including the shapes shown in FIG. 11. In an embodiment, the minimum distance between adjacent needles may be about 1.3 mm. In another embodiment, the distance between adjacent needles may be between 1.3-3.0 mm where the needle signal current or needle resistance may be varied based on needle distance while enabling a desired energy field to be formed about the needles.

In an embodiment where the distance between closest neighboring needles is shorter than 1.3 mm, there may be a risk of overheating or scaring. In an embodiment, where the distance between adjacent needles is greater than 3.0 mm, needle activation times may increases in order to achieve the same desired results as the treatment efficiency may decrease significantly. It is noted that the distance between adjacent needles may vary as function of the multiple variables discussed above.

In an embodiment other device operation factors that may vary as a function of the distance between needles including energy level (current, voltage), and a needle's thickness (outer diameter). For example, as the applied energy increases, the needle thickness may increases, the distance between adjacent needles may also be expanded to achieve a desired energy field about the needle(s). It is noted that applied energy is equal to voltage (V) multiplied by current (I) and time (t) (V*I*t).

In another embodiment the distance between adjacent needles may be reduced when the system resistance, AC frequency rate, high frequency rate, and needle length or needle depth increases in any combination. In an embodiment, the distance between adjacent needles may be determined as follows:

$$\text{Distance} = N * (\text{Power} = \text{energy}) * (\text{Needle Thickness}) * (\text{Conductivity})/(\text{Resistance}) * (\text{AC Frequency}) * (\text{High Frequency}) * (\text{Penetrated Needle Depth})$$

Where:

N: A proportional constant, Resistance: Device resistance, needle resistance, skin resistance $$\text{Energy(Joule)} = W * t (W = \text{Watt}, t = \text{time})$$
$$\text{Energy(Joule)} = V * I * t (W = V * I)$$
$$\text{Energy(Joule)} = I^2 * R * t (V = I * R)$$

Substituting Energy for V*I*t, the distance between adjacent needles may be determined as follows:

$$\text{Distance} = N * V * I * t * (\text{Needle Thickness}) * (\text{Conductivity})/(\text{Resistance}) * (\text{AC Frequency}) * (\text{High Frequency}) * (\text{Penetrated Needle Depth})$$

Other distance calculations are possible according to various embodiments. In an embodiment, a device's 100 needles 300 may fixed (distance between adjacent needles) but may move freely axially to enable movement within a confined space of the device 100.

What is claimed is:

1. A patient body treatment apparatus, comprising:
   a plurality of needles, wherein the needles are bipolar and are configured to be insertable into skin to be treated;
   a radio frequency (RF) generator configured to provide an Alternating Current (AC) RF signal to the plurality of needles,
      wherein application of the RF signal to the plurality of needles is configured to raise temperature, and
      wherein the plurality of needles is configured to treat the skin of the patient by raising temperature, and wherein the temperature rise is concentrated in an area around each needle and not between needles; and
   wherein in at least one mode of operation, the body treatment apparatus is configured to achieve coagulation of body tissue and not vaporization or carbonization of body tissue, and
   wherein the AC RF signal has a frequency, wherein the plurality of needles are arranged in a plurality of rows, and adjacent needles in each row have opposite polarities, wherein the polarities of the needles change at the frequency of the AC RF signal.

2. The apparatus of claim 1, wherein the plurality of needles are insulated.

3. The apparatus of claim 1, further comprising at least one touch screen.

4. The apparatus of claim 3, wherein the at least one touch screen further includes control of the AC RF signal and of a depth that the needles are inserted into the skin.

5. The apparatus of claim 4, wherein control of the AC RF signal comprises control of the energy level of the AC RF signal.

6. The apparatus of claim 5, wherein control of the AC RF signal comprises control of the time that the AC RF signal is applied.

7. The apparatus of claim 6, wherein control of the AC RF signal comprises control of the number of times that the AC RF signal is applied.

8. The apparatus of claim 1, further comprising an audio generation device.

9. The apparatus of claim 1, wherein the AC RF signal has a frequency of 1 to 4 Hz.

10. The apparatus of claim 1, wherein the plurality of needles comprises at least 9 needles.

11. A method of treating a patient body, comprising:
    inserting a plurality of needles into skin to be treated;
    providing an Alternating Current (AC) radio frequency (RF) signal to the plurality of needles,
       wherein each of the plurality of needles alternates in polarity, and
       wherein the AC RF signal provided to the plurality of needles raises temperature, and wherein the temperature rise is concentrated in an area around each needle and not between the needles, and
       wherein providing the AC RF signal applies energy primarily to achieve coagulation of body tissue and not vaporization or carbonization of body tissue, and
       wherein the AC RF signal has a frequency, wherein the plurality of needles are arranged in a plurality of rows, and adjacent needles in each row have opposite polarities, wherein the polarities of the needles change at the frequency of the RF signal.

12. The method of claim 11, wherein the temperature rise is concentrated around the tip of each needle.

13. The method of claim 11, further comprising controlling the AC RF signal and a depth that the needles are inserted into the skin.

14. The method of claim 13, wherein the controlling of the AC RF signal comprises controlling the energy level of the AC RF signal.

15. The method of claim 14, wherein the controlling of the AC RF signal comprises controlling the time that the AC RF signal is applied.

16. The method of claim 15, wherein the controlling of the AC RF signal comprises controlling the cycles of application of the AC RF signal.

17. The method of claim 16, wherein the AC RF signal has a frequency of 1 to 4 Hz.

* * * * *